(12) United States Patent
Bonney et al.

(10) Patent No.: US 7,621,300 B2
(45) Date of Patent: Nov. 24, 2009

(54) METERING METHOD FOR PARTICULATE MATERIAL

(75) Inventors: Stanley George Bonney, Ware (GB); Howard Peter Duffield, Ware (GB)

(73) Assignee: Glaxo Group Limited, Greenford, Middlesex (GB)

( * ) Notice: Subject to any disclaimer, the term of this patent is extended or adjusted under 35 U.S.C. 154(b) by 839 days.

(21) Appl. No.: 10/475,393

(22) PCT Filed: Mar. 25, 2002

(86) PCT No.: PCT/EP02/03325

§ 371 (c)(1),
(2), (4) Date: Oct. 17, 2003

(87) PCT Pub. No.: WO02/086427

PCT Pub. Date: Oct. 31, 2002

(65) Prior Publication Data

US 2004/0168739 A1 Sep. 2, 2004

(30) Foreign Application Priority Data

Apr. 20, 2001 (GB) .................. 0109871.4
Oct. 9, 2001 (GB) .................. 0124187.6

(51) Int. Cl.
*B65B 1/04* (2006.01)

(52) U.S. Cl. .................. 141/83; 141/237; 141/325; 53/282

(58) Field of Classification Search .............. 141/1, 141/83, 237, 325; 427/2.14, 294–298, 180, 427/185; 53/282; 424/17
See application file for complete search history.

(56) References Cited

U.S. PATENT DOCUMENTS

| | | | | |
|---|---|---|---|---|
| 2,170,469 | A * | 8/1939 | Carter | 141/7 |
| 2,540,059 | A | 1/1951 | Stirn et al | |
| 3,645,303 | A * | 2/1972 | Carter | 141/7 |
| 3,693,672 | A * | 9/1972 | Hiland | 141/7 |
| 3,718,164 | A * | 2/1973 | Stewart | 141/1 |
| 3,832,827 | A * | 9/1974 | Lemelson | 53/111 R |
| 3,874,431 | A | 4/1975 | Aronson | |
| 3,911,972 | A * | 10/1975 | Hubers et al. | 141/7 |
| 4,084,626 | A * | 4/1978 | King | 141/7 |
| 4,262,708 | A * | 4/1981 | de Echeandia et al. | 141/7 |
| 4,275,544 | A * | 6/1981 | Hisazumi et al. | 53/433 |
| 4,509,568 | A | 4/1985 | Kawaguchi et al. | |
| 4,640,322 | A | 2/1987 | Ballester | |
| 4,662,915 | A | 5/1987 | Shirai et al. | |
| 4,764,056 | A | 8/1988 | Zentgraf et al. | |
| 4,776,493 | A * | 10/1988 | Tegel | 222/196 |
| 4,966,204 | A * | 10/1990 | Pedigo | 141/7 |
| 5,072,574 | A * | 12/1991 | Puett | 53/427 |
| 5,187,921 | A * | 2/1993 | Wilson et al. | 53/453 |
| 5,246,042 | A * | 9/1993 | Farrell | 141/59 |
| 5,339,871 | A * | 8/1994 | Collins et al. | 141/1 |
| 5,360,141 | A | 11/1994 | Scatizzi | |
| 5,379,572 | A * | 1/1995 | Giovannone | 53/478 |
| 5,522,555 | A | 6/1996 | Poole | |
| 5,549,144 | A * | 8/1996 | Dworak et al. | 141/146 |
| 5,590,509 | A * | 1/1997 | Esteves et al. | 53/432 |
| 5,743,049 | A * | 4/1998 | Thallemer | 52/2.21 |
| 5,765,607 | A * | 6/1998 | Ansaloni | 141/135 |
| 5,775,389 | A * | 7/1998 | Griffin | 141/325 |
| 5,783,273 | A * | 7/1998 | Yamamoto et al. | 428/35.9 |
| 5,826,633 | A * | 10/1998 | Parks et al. | 141/18 |
| 5,937,618 | A * | 8/1999 | Chandler | 53/427 |
| 5,971,037 | A * | 10/1999 | Ansaloni | 141/83 |
| 6,024,141 | A * | 2/2000 | Wegman | 141/59 |
| 6,035,905 | A * | 3/2000 | Griffin | 141/181 |
| 6,146,685 | A * | 11/2000 | Chrai et al. | 427/2.14 |
| 6,182,712 | B1 * | 2/2001 | Stout et al. | 141/18 |
| 6,226,962 | B1 * | 5/2001 | Eason et al. | 53/471 |
| 6,237,650 | B1 * | 5/2001 | Ansaloni | 141/237 |
| 6,267,155 | B1 * | 7/2001 | Parks et al. | 141/18 |
| 6,311,743 | B1 * | 11/2001 | Baroncini | 141/234 |
| 6,397,840 | B1 * | 6/2002 | Chrai et al. | 128/202.25 |
| 6,397,901 | B1 * | 6/2002 | Saito et al. | 141/32 |
| 6,581,650 | B2 * | 6/2003 | Parks et al. | 141/12 |
| 6,684,917 | B2 * | 2/2004 | Zhu et al. | 141/18 |
| 6,691,747 | B1 * | 2/2004 | Marcus et al. | 141/7 |
| 2001/0047837 | A1 * | 12/2001 | Parks et al. | 141/18 |
| 2002/0017295 | A1 * | 2/2002 | Weers et al. | 128/203.12 |

FOREIGN PATENT DOCUMENTS

| | | |
|---|---|---|
| CA | 949786 | 6/1974 |
| EP | 0768122 | 4/1997 |
| EP | 0962258 | 5/1999 |
| GB | 1309424 | 3/1970 |
| GB | 2033330 | 5/1980 |
| GB | 2184086 A * | 6/1987 |
| JP | 62201729 A * | 9/1987 |

(Continued)

*Primary Examiner*—Sikarl A Witherspoon
(74) *Attorney, Agent, or Firm*—Dwight S. Walker

(57) ABSTRACT

There is provided a method for metering a quantity of a particulate material onto the surface of a porous retainer comprising the steps of: exposing a first surface of a porous retainer to a pool of particulate material; applying a vacuum to a second surface of the porous retainer to meter material on the first surface; and adjusting the level of the vacuum to regulate the quantity of material metered on the retainer.

20 Claims, 4 Drawing Sheets

FOREIGN PATENT DOCUMENTS

| | | |
|---|---|---|
| WO | 8302433 | 7/1983 |
| WO | 9919215 | 4/1999 |
| WO | 0009249 | 2/2000 |
| WO | 0009254 | 2/2000 |
| WO | 0027456 | 5/2000 |

* cited by examiner

METERING METHOD FOR PARTICULATE MATERIAL

CROSS-REFERENCE TO RELATED APPLICATIONS

This application is filed under 35 U.S.C. § 371 as the United States National Phase Application of International Application No. PCT/EP02/03325 filed Mar. 25, 2002 claiming priority from Great Britain Application Nos. 0109871.4 and 0124187.6 filed, Apr. 20, 2001 and Oct. 9, 2001 respectively.

TECHNICAL FIELD

The present invention relates to a method of metering particulate material onto the surface of a porous retainer. The method is particularly useful for filling blister strips and primary packs with powdered medicaments.

BACKGROUND TO THE INVENTION

Many chemical products are produced in the form of tablets or as fine, dry powders. It is often highly desirable to package pre-determined amounts of such chemicals for ease of utilisation by end users. Typical examples would be in the biocidal and pesticide industries, where specific quantities of particular products are pre-packed for both convenience and safety reasons. Pre-packaging of specified amounts of hazardous products, such as toxic chemicals, reduces operator error and minimises chemical handling risks inherent in further weighing or dilution operations with such chemicals.

In the medical field, the delivery of an accurate, pre-determined dose of medicament to a patient is critical to effective treatment of disease. The majority of drugs are now prescribed to patients in packages containing many unit treatments of particular medicaments. This pre-packaging of known quantities of medicaments facilitates the accurate administration of drugs to a patient by simplifying the process and minimising the risk of patient error. Thus many medicaments are provided in blister packs, where each blister contains a unit dose in tabular or powder form.

Pulmonary drug delivery systems depend upon the administration of effective doses of medicament to the lungs of a patient and rely upon inhalation of a drug dispersion or aerosol. A variety of medical devices are used to administer such medicaments, ranging from nebulisers, metered dose inhalers (MDI's) and dry powder inhalers (DPI's). The latter are of particular interest to the present invention, as they rely upon the delivery of fine dry powders which are often stored within a unit dose receptacle such as a blister pack within the device.

There are many technical problems in filling receptacles, including unit-dose receptacles such as blister packs, with powdered medicament. Fine powders can be difficult to manipulate and measure, particularly when flow properties of the powder vary due to agglomerisation or clumping of the powder. The presence of clumps in powders leads to inaccuracies in the quantities of powder dispensed into receptacles which rely upon gravimetric and/or volumetric methods. Thus the metering of fine powders presents many technical problems in terms of basic handling and weighing/measuring operations associated with dispensing such powders into appropriate receptacles.

Several approaches to addressing these problems are apparent from the literature. Thus U.S. Pat. No. 4,640,322 discloses a device which uses a negative pressure to draw powder from a hopper to a measuring chamber. An alternative method, involving a stirring mechanism, is described in U.S. Pat. No. 2,540,059, wherein powder undergoes stirring prior to pouring into a metering chamber. Other methods range from taking cores from a powder reservoir for filling capsules (U.S. Pat. No. 3,874,431) to applying a vacuum to fill measuring chambers with powder (Canadian Patent Number 949,786).

The Applicant has found that particulate material can be metered onto a first surface of a porous retainer or substrate by the application of a vacuum to a second surface. This method is particularly effective for metering powdered material which has been fluidised by aeration in a fluid powder bed. The particulate material can then be hermetically sealed in place on the porous retainer with a suitable metallic foil, plastic film or organo-metallo laminate, to form a blister or primary pack for use in a DPI device.

SUMMARY OF INVENTION

According to the present invention there is provided a method for metering a quantity of a particulate material onto a porous retainer comprising: exposing a first surface of the porous retainer to the particulate material; applying a vacuum to a second surface of the porous retainer to meter material onto the first surface; and adjusting the vacuum to regulate the quantity of material metered onto the first surface of the retainer.

Regulation of the quantity of material metered onto the retainer may be effected by controlling the duration and/or force of the vacuum, or negative pressure. The area, porosity and physical properties of the retainer to which the vacuum is applied will also affect the quantity of particulate material metered onto the retainer surface. Both volumetric and gravimetric means may be used to determine the quantity of particulate material metered onto the retainer surface.

In one aspect, the particulate material is in the form of a fine powder. In aspects, the fine powder is in bulk form (e.g. in the form of a powder bed) or is aerosolised or fluidised by any suitable means prior to application to the porous retainer.

In another aspect, the fine powder comprises particles having a mean diameter ranging from 1 µm to 100 µm.

In a further aspect, the particles are fluidised by aeration.

Preferably, the fine powder is in the form of a cloud.

In one aspect, the retained particulate material is subsequently subjected to a compressive force (e.g. in a tabletting formation step).

In another aspect, the composition of the porous retainer is selected from the group consisting of metal, alloy, silicate and organic polymer. Suitable organic polymers include fluorocarbon polymers, such as those based upon polytetrafluoroethylene as described in U.S. Pat. No. 4,196,070. Suitable metallic materials include sintered refractory metal oxides such as silica alumina, titania, zirconia and tungsten oxides (as described in U.S. Pat. No. 4,973,435).

Preferably, the physical structure of the retainer is selected from the group consisting of meshed, sintered, woven, pierced, cast and foamed. Meshed structures are irregular in nature, comprising a random lattice of fibres.

Preferably, the pierced structure is created by drilling the retainer with a laser beam. The beam can be generated by any source suitable for generating laser energy, including carbon dioxide, diode, fibre and copper vapour laser sources. The laser beam can also be generated by a Q-switched Neodymium Yttrium Aluminium Garnate laser source. Typically the maximum average power is from 10 W to 200 W, preferably from 25 W to 100 W and the maximum peak power is from 10 kW to 1 kW, preferably from 5 kW to 3 kW.

Preferably, the pierced structure is created by chemical etching of the retainer. Chemical etching means are well known in the art, utilising a range of acids, alkalis and oxidising agents to wet etch materials under defined thermal conditions.

Preferably, the pierced structure is created by electro discharge machining of the retainer. This technique involves electrochemical dissolution of metal ions from the retainer surface using suitable electrolytes under high current/low voltage conditions.

More preferably, the porous retainer is in the form of a sieve selected from the group consisting of membrane, filter, screen, mesh and strainer.

In a further aspect, the vacuum is applied by a vacuum orifice block.

Preferably the level of the vacuum is monitored by a pressure sensor. More preferably, the pressure sensor comprises a pressure transducer.

More preferably, the level of the vacuum is adjusted by means of an airflow control valve.

In one aspect, a control device which communicates with the pressure sensor and the airflow control valve regulates the level of the vacuum.

Preferably, the control device is selected from the group consisting of computer, personal computer and programmable logic controller (PLC).

In another aspect, the quantity of particulate material metered on the retainer is in the range of 1 μg to 100 mg. Preferably, the quantity of particulate material metered is in the range 1 μg to 1 mg.

In a further aspect, the method additionally comprises covering the first surface of the porous retainer with a perforated mask.

In another aspect of the present invention there is provided a method for loading a medicament container with particulate material, the method comprising the steps of: metering the particulate material on a porous retainer according to the method as hereinbefore described; and placing the retainer within the medicament container.

Preferably, the medicament container is selected from the group consisting of bottle, vial, medicament pack and blister strip.

Preferably, the method additionally comprises sealing the medicament container with one or more seals. Preferably, the one or more seals is selected from the group consisting of lid, top, base, film, foil and laminate.

Suitably sealing materials include metals, alloys and organic polymers. Organic polymeric films may, for example, comprise polyethylene, polypropylene, polyvinyl chloride or polyethylene terephthalate. Suitable metallic foils include aluminium and tin foils, typically having a thickness ranging from 5 μm to 100 μm.

Preferably the method comprises sealing the first and second surfaces of the container with an organic polymeric metallic laminate. Such laminates comprise one of more layers of a suitable organic polymer bonded to a metallic foil, such as aluminium foil.

In one aspect, the particulate material comprises a medicament. Preferably, the medicament is selected from the group consisting of albuterol, salmeterol, fluticasone propionate and beclomethasone dipropionate and salts or solvates thereof and any mixtures thereof.

In one aspect, the medicament container is a tabletting mould (e.g. in a tabletting press). In this case, the method additionally comprises a tabletting compression step to form a tablet.

In a further aspect of the present invention, there is provided a medicament pack or blister strip obtainable by any of the methods hereinbefore described.

DETAILED DESCRIPTION OF DRAWINGS

Figure 1A:
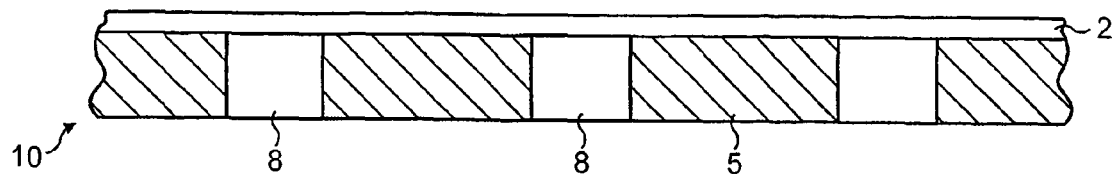
FIGS 1a-1d show a porous retainer at various stages of loading with powdered medicament, according to the method of the present invention.

FIG. 1a shows one embodiment of a porous retainer 10. The retainer 10 is composed of a porous body 2 and a mask 5 which defines an aperture 8 for receipt of particulate material, such as a powdered medicament. The mask 5 comprises a non-porous material, such as an organic polymer or metal. The porous body 2 may be composed of any porous material, such as sintered or meshed material.

Figure 1B:
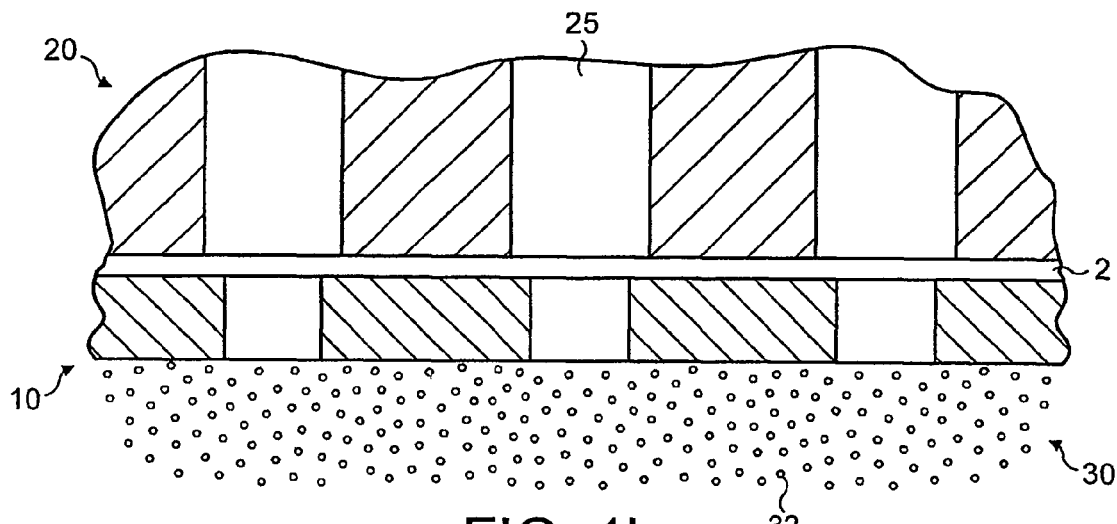
Figure 1C:
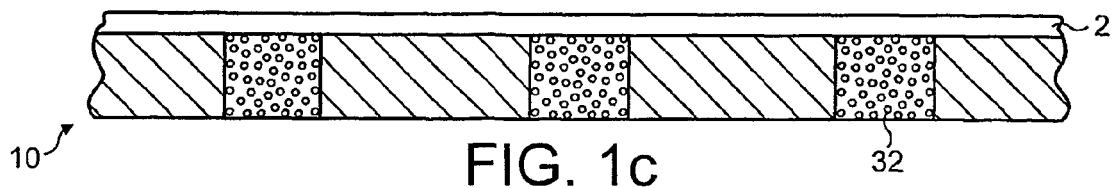
Figure 1D:
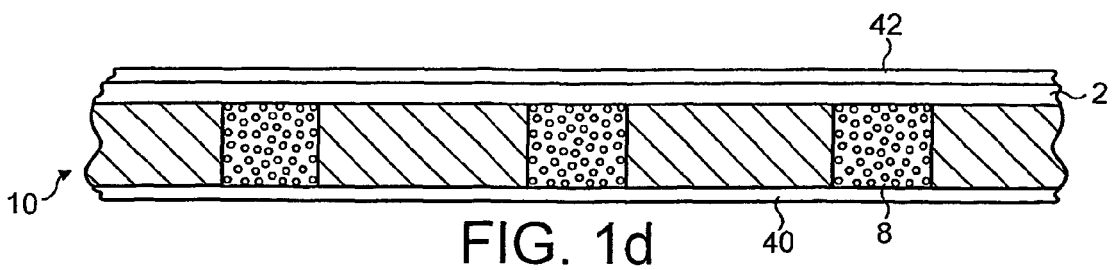

In FIG. 1b, the retainer 10 is connected to a vacuum orifice block 20 that exerts a negative pressure through channel 25 on the retainer body 2. A cloud 30 of powdered medicament 32 is exposed to the vacuum through the porous body 2 of the retainer. The cloud 30 of medicament powder 32 may be generated by, for example, a fluidised bed. Alternatively, the cloud may be generated by electrostatic or vibrationary means.

Medicament powder 32 is thus drawn into the aperture 8 and tightly packed together under vacuum (FIG. 1*c*). The retainer may then be completely sealed to prevent ingress of moisture or dust with appropriate organic polymeric or metallic materials (FIG. 1*d*). A first seal 40 is positioned over the surface of the retainer which bears apertures 8 containing medicament powder 32, while a second seal 42 is applied across the exterior surface of the porous body 2. Examples of suitable sealing materials include organic polymers such as polyethylene, polypropylene, polyvinyl chloride or polyethylene terephthalate, and metallic foils such as aluminium or tin foil. Alternatively, laminates comprising organic polymeric films bonded to metallic foils may be used to seal the retainer.

FIG. 2 is a cross-sectional view of an apparatus used to meter powdered medicament on a porous retainer. Porous retainer 102 is positioned on a first face of vacuum orifice block 120 and a non-porous mask 105 superimposed on the second face of retainer 102. The mask 105 has an aperture 108 cut within it. A cloud 130 of powdered medicament 132 is then generated next to the mask 105 and a negative pressure exerted on it by the vacuum orifice block 120. The vacuum or negative pressure is applied to the medicament 132 via channel 125, porous retainer 102 and aperture 108. The vacuum draws material 132 into the aperture 108, the rate and extent of filling of the aperture 108 being dependent upon the force and duration of the vacuum applied. Regulation of the metering or filling process is effected by control device 150 which is in communication with a pressure sensor 155 (such as a pressure transducer) and an airflow control valve 158. At a pre-set time and/or pressure (as indicated by pressure sensor 155), the control device 150 will adjust the level of the vacuum being exerted on the cloud 130 by regulating the air flow control valve 158 to reduce the vacuum and complete the metering/filling process.

Figure 2:
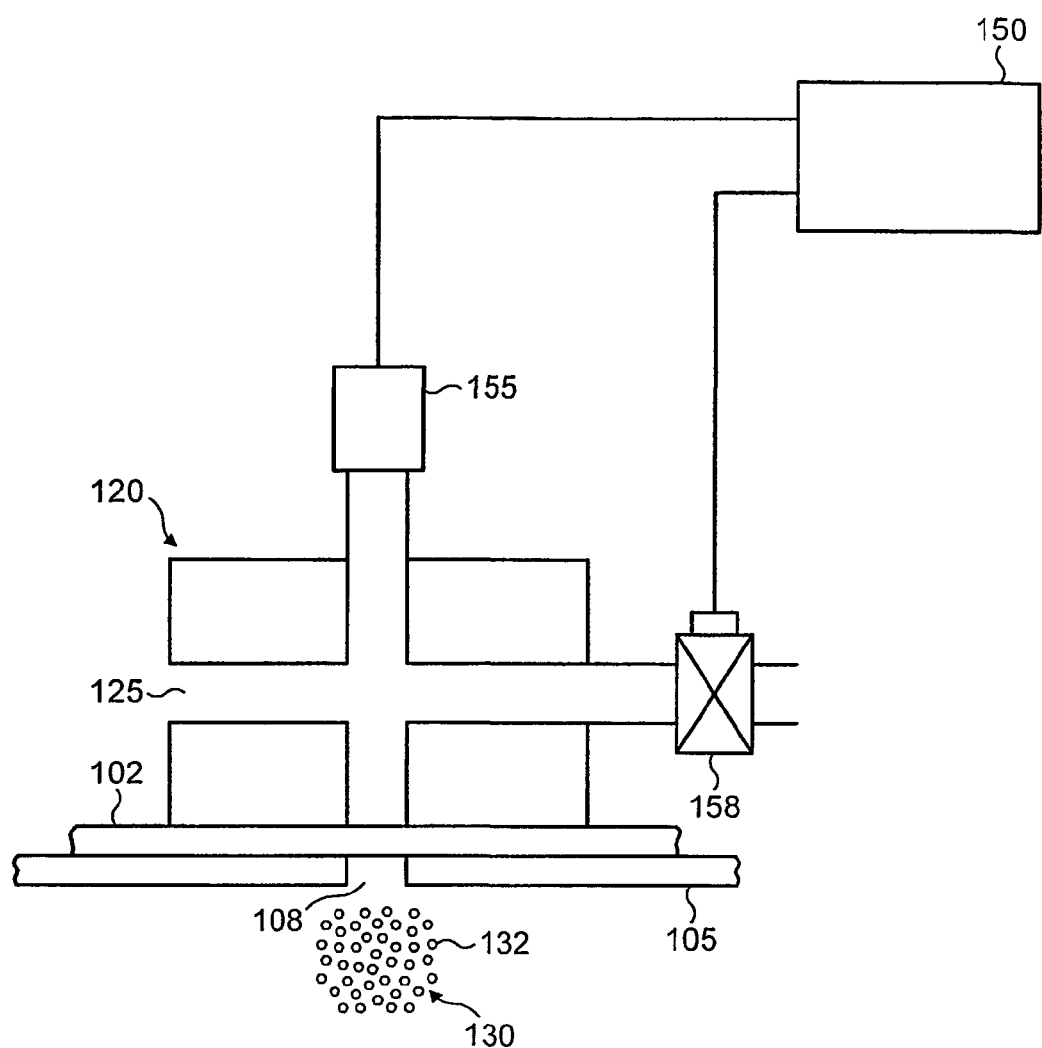
FIG. 2 is a cross-sectional representation of powdered medicament being metered on a porous retainer, according to the method of the present invention.
Figure 3:
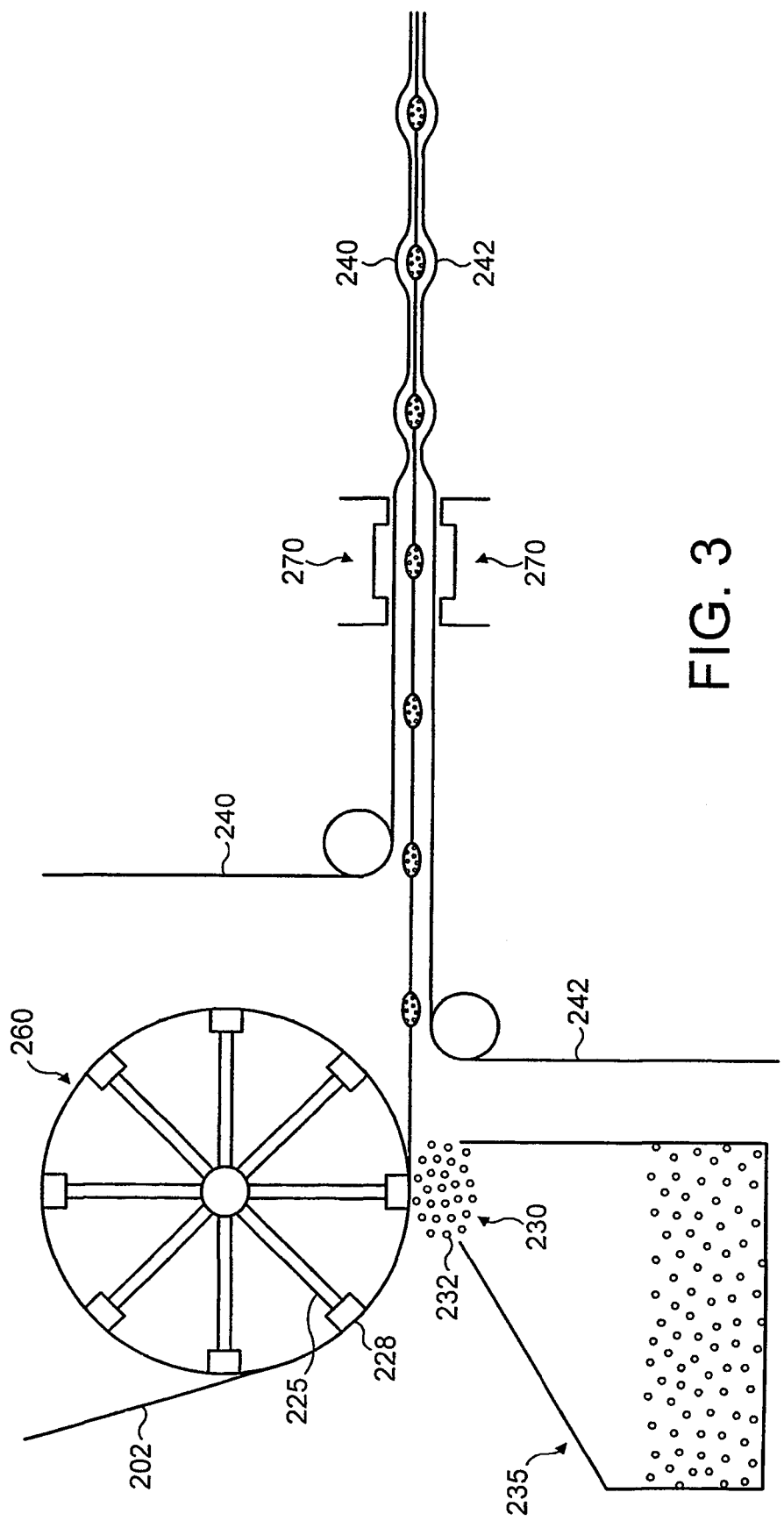
FIG. 3 depicts the process whereby powdered medicament is metered on a porous retainer then sealed with metallic foil or a plastic film.

FIG. 3 illustrates a continuous process whereby powdered medicament is metered on a porous retainer and sealed. An elongate porous substrate or body 202 is fed onto a rotary metering drum 260 which comprises the apparatus of FIG. 2. A vacuum system, under the regulation of a control device (not shown), exerts a negative pressure on a cloud 230 of powdered medicament 232 through channel 225 and port 228 through porous body 202. Powdered medicament 232 from cloud 230, which is generated in fluidised bed 235, will be drawn by the vacuum onto the body of the porous retainer. The porous substrate 202 may, or may not, be over-layered with a perforated non-porous mask (not shown) which defines the volume of powdered medicament metered onto the substrate. In the absence of such a mask, the quantity of medicament metered on the substrate is dependent upon the area of the vacuum port 228 and the porosity of the substrate material.

Once medicament is trapped on the substrate 202, the substrate is conveyed to a sealing station 270 where it is completely encased by a first 240 and a second 242 seal using adhesive or heating means. Such seals may comprise organic polymeric (e.g. polyethylene, polypropylene, polyvinyl chloride or polyethylene terephthalate) or metallic (e.g. aluminium or tin) sheets/foils. Alternatively, laminated sheets comprised of both organic polymers and metal foil may be used as seals. The sealing process prevents moisture and/or dust ingress. The sealed substrates may take the form of a blister strip or roll, or a primary pack.

As shown in the diagram, the process is continually repeated as the rotary metering drum 260 collects more medicament powder on the porous retainer 202 and delivers it to station 270 to be hermetically sealed.

In alternative embodiment of the process of FIG. 3, powdered medicament is continuously fed to the porous retainer 202 of the vacuum filling port 228 by the action of a stainless steel belt. The belt is driven by a continous rotary feed and powder is delivered to the belt by the action of a powder feed acting under gravity.

Figure 4A:
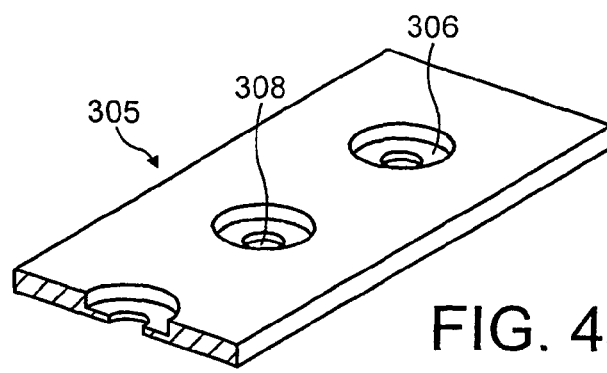
FIGS. 4a-c illustrate the component parts of a blister strip and primary pack loaded with powdered medicament, according to the present invention.
Figure 4B:
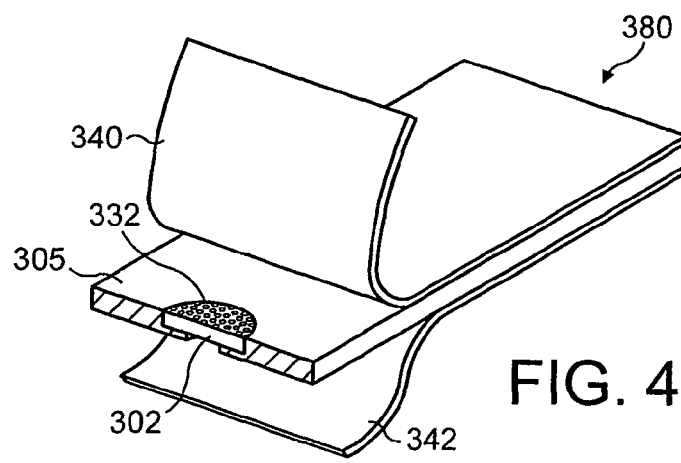
Figure 4C:
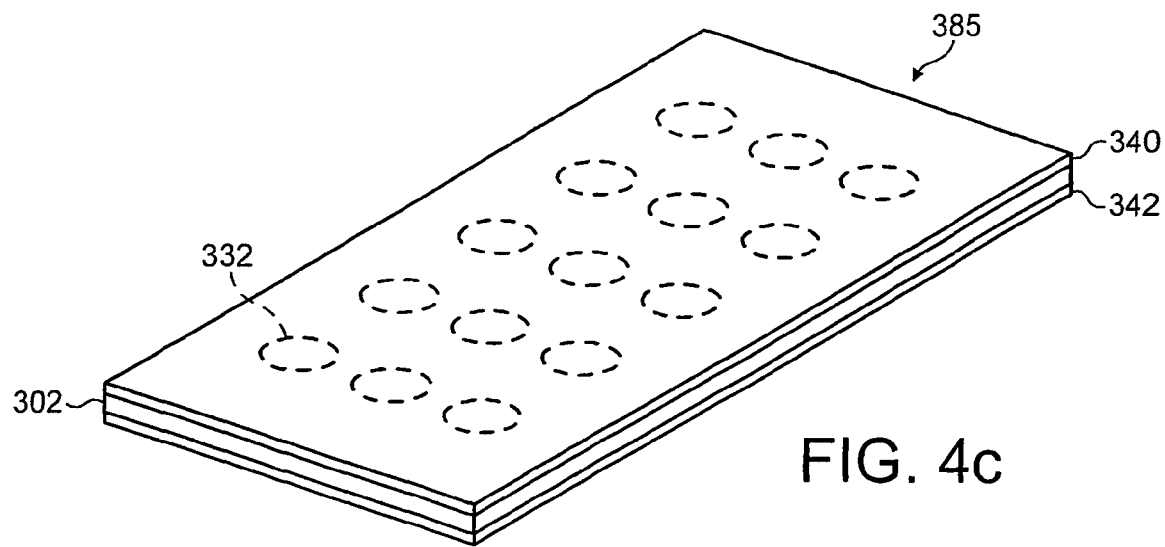

FIGS. 4*a-c* depict the component parts of blister strips and primary packs suitable for use in dry powder inhalation devices. Thus FIG. 4*a* shows a blister strip mask 305 having a cavity 306 designed for receipt of a porous disc (not shown). The mask is composed of a non-porous material, such as an organic polymer, and the cavity 306 has an aperture 308 therein. The porous disc may be inserted in the cavity 306 and loaded with medicament powder (not shown) by the application of a vacuum to the aperture, as illustrated in FIGS. 1-3.

FIG. 4*b* depicts a blister strip 380 composed of the mask 305 of FIG. 4*a* loaded with powdered medicament 332. Seals 340 and 342 are peeled back in the diagram to reveal the porous disc 302 containing powdered medicament 332. The seals 340 and 342 may comprise sheets of a suitable organic polymer and/or metallic film or laminated sheets of both materials.

FIGS. 4*c* illustrates a primary pack 385 containing multiple doses of medicament powder 332. The pack 385 is composed of a porous substrate 302 sealed by an organic metallic laminated foil 340, and an organic polymeric sheet 342.

Figure 5:
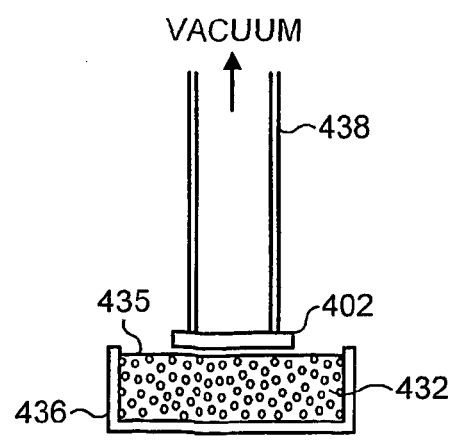
FIG. 5 shows a process whereby a porous retainer is exposed to a bulk powder bed.

FIG. 5 shows an alternative filling process herein. Bulk powdered medicament 432 is comprised as a levelled powder bed 435 in powder bowl 436. A first surface of a porous substrate 402 is bought into either close proximity or direct contact with the levelled powder bed 435. A vacuum is applied to the reverse surface of the substrate 402 by the action of vacuum pipe 438 driven by a vacuum pump (not shown). The amount of powdered medicament 432 impregnated on the porous retainer 402 is regulated by control of the vacuum (e.g. time of applying vacuum and/or vacuum force applied).

The invention is suitable for filling blister packs, primary packs or other suitable containers with powdered medicament or tablets, particularly for the treatment of respiratory disorders. The invention is also suitable for filling tubes or other suitable containers with powdered medicament for the treatment of respiratory disorders to be used in a drug delivery system (e.g. an inhalation device). Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate, ketotifen or nedocromil; antiinfectives e.g., cephalosporins, penicillins, streptomycin, sulphonamides, tetracyclines, zanamivir and pentamidine; antihistamines, e.g., methapyrilene; anti-inflammatories, e.g., beclomethasone dipropionate, fluticasone propionate, flunisolide, budesonide, rofleponide, mometasone furoate, ciclesonide or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol or 4-hydroxy-7-[2-[[2-[[3-(2-phenylethoxy) propyl] sulfonyl] ethyl]amino]ethyl-2(3H)-benzothiazolone; diuretics, e.g., amiloride; anticholinergics, e.g., ipratropium, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salmeterol, ipratropium bromide, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) in combination with an anti-inflammatory steroid such as a beclomethasone ester (e.g., the dipropionate) or a fluticasone ester (e.g., the propionate). A particularly preferred combination comprises salmeterol xinafoate salt and fluticasone propionate.

It may be appreciated that any of the parts of the apparatus that contact the powder or tablet may be coated with materials such as fluoropolymer materials which reduce the tendency of medicament to adhere thereto. Suitable fluoropolymers include polytetrafluoroethylene (PTFE) and fluoroethylene propylene (FEP). Any movable parts may also have coatings applied thereto which enhance their desired movement characteristics. Frictional coatings may therefore be applied to enhance frictional contact and lubricants used to reduce frictional contact as necessary.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims or may include, by way of example and without limitation, one or more of the following claims:

The invention claimed is:

1. A method for loading a medicament container with discrete metered quantities of a particulate material comprising a medicament, the medicament container comprising a porous retainer having first and second surfaces and at least one seal, said method comprising:
   providing the porous retainer;
   exposing the first surface of said porous retainer to a source of said particulate material;
   controllably applying a vacuum to the second surface of the porous retainer to meter a quantity of the particulate material from the source onto said first surface at discrete sites thereon; and
   applying the at least one seal to said porous retainer to seal the metered quantities at the discrete sites on the porous retainer and so load said medicament container.

2. A method according to claim 1, wherein the particulate material is in the form of a fine powder.

3. A method according to claim 2, wherein said fine powder comprises particles having a mean diameter ranging from 1 µm to 100 µm.

4. A method according to claim 1, wherein the source of fine powder is in the form of a cloud.

5. A method according to claim 1, wherein the source of particulate material is in the form of a bulk powder bed.

6. A method according to claim 1, wherein the composition of the porous retainer is selected from the group consisting of metal, alloy, silicate and organic polymer.

7. A method according to claim 1, wherein the physical structure of the retainer is selected from the group consisting of meshed, sintered, woven, pierced, cast and foamed.

8. A method according to claim 1, wherein the porous retainer is in the form of a sieve selected from the group consisting of membrane, filter, screen, mesh and strainer.

9. A method according to claim 1, wherein said vacuum is applied by a vacuum orifice block.

10. A method according to claim 1, wherein the level of the vacuum is monitored by a pressure sensor.

11. A method according to claim 10, wherein said pressure sensor comprises a pressure transducer.

12. A method according to claim 1, wherein the level of the vacuum is adjusted by means of an airflow control valve.

13. A method according to claim 1, wherein a control device which communicates with the pressure sensor and said airflow control valve regulates the level of the vacuum.

14. A method according to claim 1, wherein said control device is selected from the group consisting of computer, personal computer and programmable logic controller (PLC).

15. A method according to claim 1, wherein the quantity of particulate material metered on the retainer is in the range of 1 µg to 100 mg.

16. A method according to claim 15, wherein said quantity of particulate material metered is in the range of 1 µg to 1 mg.

17. A method for loading a medicament container with discrete metered quantities of a particulate material comprising a medicament, the medicament container comprising:
   a porous retainer having a porous body which has first and second surfaces, the first surface forming a second outer surface of the retainer, and a perforated mask having first and second surfaces and plurality of perforations extending therebetween, the first surface of the mask overlying the second surface of the porous body and the second surface of the mask forming a first outer surface of the porous retainer, and
   at least one seal,
   said method comprising:
   providing the porous retainer;
   exposing the first outer surface of said porous retainer to a source of said particulate material;
   controllably applying a vacuum to the second outer surface of the porous retainer to meter a quantity of the particulate material in said source into said perforations; and
   applying the at least one seal to the porous retainer to seal the metered quantities in the perforations and so load said medicament container.

18. A method according to claim 1, wherein the medicament container is selected from the group consisting of a medicament pack and a blister strip.

19. A method according to claim 17, wherein said at least one seal is selected from the group consisting of film, foil and laminate.

20. A method for loading a medicament container with discrete metered quantities of a particulate material comprising a medicament, said medicament container comprising a porous retainer having first and second surfaces and at least one seal, said method comprising:
   providing the porous retainer;
   exposing the first surface of said porous retainer to a source of particulate material, wherein said source of particulate material is present in aerosolized or fluidized form;
   controllably applying a vacuum to the second surface of the porous retainer to meter a quantity of the particulate material from the source onto said first surface at discrete sites thereon; and
   applying at least one seal to said porous retainer to seal the metered quantities at the discrete sites on the porous retainer and so load said medicament container.

* * * * *